(12) United States Patent
Fugo

(10) Patent No.: US 8,088,126 B2
(45) Date of Patent: *Jan. 3, 2012

(54) METHOD AND APPARATUS FOR PLASMA INCISION OF CARDIOVASCULAR TISSUE

(76) Inventor: Richard J. Fugo, Plymouth Meeting, PA (US)

( * ) Notice: Subject to any disclaimer, the term of this patent is extended or adjusted under 35 U.S.C. 154(b) by 1088 days.

This patent is subject to a terminal disclaimer.

(21) Appl. No.: 11/891,838

(22) Filed: Aug. 13, 2007

(65) Prior Publication Data

US 2008/0045941 A1 Feb. 21, 2008

Related U.S. Application Data

(60) Provisional application No. 60/838,191, filed on Aug. 17, 2006.

(51) Int. Cl.
*A61B 18/18* (2006.01)
(52) U.S. Cl. .................. 606/38; 606/34; 606/39
(58) Field of Classification Search ............. 606/42, 606/45
See application file for complete search history.

(56) References Cited

U.S. PATENT DOCUMENTS

| | | |
|---|---|---|
| 3,663,858 A | 5/1972 | Lisitano |
| 3,903,891 A | 9/1975 | Brayshaw |
| 4,461,688 A | 7/1984 | Morrison, Jr. |
| 4,599,134 A | 7/1986 | Babu |
| 4,691,090 A | 9/1987 | Garlanov et al. |
| 4,855,563 A | 8/1989 | Beresnev |
| 5,047,649 A | 9/1991 | Hodgson et al. |
| 5,108,391 A | 4/1992 | Flachenecker et al. |
| 5,217,457 A | 6/1993 | Delahuerga et al. |
| 5,235,155 A | 8/1993 | Yamada |
| 5,300,068 A | 4/1994 | Rosar |
| 5,346,491 A | 9/1994 | Oerti |
| 5,518,597 A | 5/1996 | Storer et al. |
| 5,558,671 A | 9/1996 | Yates |
| 5,591,301 A | 1/1997 | Grewal |
| 5,599,344 A | 2/1997 | Paterson |
| 5,628,745 A | 5/1997 | Bek |
| 5,647,869 A | 7/1997 | Goble |
| 5,669,907 A | 9/1997 | Platt |
| 5,669,975 A | 9/1997 | Ashtiani |
| 5,958,266 A | 9/1999 | Fugo et al. |
| 6,135,998 A | 10/2000 | Palanker |
| 6,142,992 A | 11/2000 | Cheng et al. |
| 6,190,382 B1 | 2/2001 | Ormsby et al. |
| 6,479,785 B1 | 11/2002 | Fugo et al. |
| 6,663,625 B1 | 12/2003 | Ormsby et al. |
| 6,787,730 B2 | 9/2004 | Coccio et al. |
| 6,867,387 B2 | 3/2005 | Fugo et al. |
| 7,004,938 B2 | 2/2006 | Ormsby et al. |
| 7,015,037 B1 | 3/2006 | Furcht et al. |

(Continued)

OTHER PUBLICATIONS

Kemp, W., *NMR in Chemistry: A Multinuclear Introduction*, Macmillan Publishing Co., pp. 1-28, 1988.

(Continued)

*Primary Examiner* — Linda Dvorak
*Assistant Examiner* — Jaymi Della

(57) ABSTRACT

An apparatus and method for performing surgery using plasma is described. In one exemplary embodiment, the apparatus includes a radiofrequency signal generator, a conditioning network coupled to the radiofrequency signal generator, and a catheter coupled to the conditioning network, the catheter including at least one electrode, such that the conditioning network conditions radiofrequency energy produced by the radiofrequency signal generator to create plasma at the at least one electrode of the catheter.

10 Claims, 4 Drawing Sheets

U.S. PATENT DOCUMENTS

| | | | |
|---|---|---|---|
| 7,070,595 | B2 | 7/2006 | Ormsby et al. |
| 7,104,989 | B2 | 9/2006 | Skards |
| 2001/0012934 | A1 | 8/2001 | Chandrasekaram et al. |
| 2002/0060207 | A1* | 5/2002 | Coccio et al. ............ 219/121.52 |

OTHER PUBLICATIONS

Oler, R.C., "The 160 Meter Band: An enigma shrouded in mystery—Part I," Amateur Radio CQ, vol. 54, No. 3, pp. 9-14, Mar. 1998.

Staar Surgical symposium, "Plate Haptic Lens Implantation Techniques . . . The Bridge to the Future," R.J. Fugo, MD, PhD. the Plasma Blade, San Francisco, CA, Oct. 25, 1997.

ASCO Lecture Symposium, R.J. Fugo, MD, PhD, "The Plasma Blade," San Francisco, CA, Oct. 26, 1997.

Fugo, R.J., et al., "Devices Hone Electromagnetic Field Surgery: Plasma Blade Incises Tissue: Smart Blade Guides Path," Opthalmology Times, vol. 23, No. 3, pp. 4-5, Jan. 25, 1998.

ACES Lecture Symposium, Quality Surgery 12, R.J. Fugo, MD, PhD. "Electromagnetic Phacoemulsification," Lake Buena Vista, FL, Feb. 13, 1998.

Eyeworld editorial, "In Praise of the Pioneering Spirit," p. 5, "The Never Ending Quest: Creating a Better Way to Remove the Lens," pp. 50-51; "The Leading Edge: Harnessing Electrons for a Faster, Smarter Incision," p. 88, vol. 3, No. 4, Apr. 1988.

Friedman, Joshua, *The Technical Aspects of Electrosurgery*, J. Oral Surgery, vol. 36, No. 2, pp. 177-187, 1973.

Besancon, Robert M. ed., *The Encyclopedia of Physics*, $2^{nd}$ ed., Van Nostrand Reinhold Co. pp. V-XIII; 851-853, 1974.

Sozio, Ralph B. et al. "A Histologic & Electronic Evaluation of Electrosurgical Currents: Non-Filtered Full-wave Modulated vs. Filtered Current," Journal of Prosthetic Dentistry, pp. 300-311, Mar. 1975.

Maness, W. L., et al., "Histologic Evaluation of Electrosurgery with Varying Frequency and Waveform," Journal of Prosthetic Dentistry, vol. 40, No. 3, pp. 304-308, 1978.

Krause-Hohnestein, U., *Electrosurgery: Fundamental Requirements for Use*, Quintessense International Nov. 1983, pp. 1115-1124.

Chen, Francis F., *Introduction to Plasma Physics & Controlled Fusion*, Plenum Publishing Co., pp. I-XV, 1-17, 1983.

Ichimaru, Setsuo, *Statistical Plasma Physics, vol. 1: Basic Principles*, Addison Wesley Publishing Co., pp. I-XIX, 1-28, 1992.

Ichimaru, Setsuo, *Statistical Plasma Physics, vol. 1: Basic Principles*, Addison Wesley Publishing Co., pp. 323-359, 1992.

Ferris, Daron G., et al., "Gynecologic & Dermatologic Electrosurgical Units: A Comparative Review," Journal of Family Practice, vol. 39, No. 2, pp. 160-169, 1994.

The Lincoln Electric Co., "The Procedure Handbook of Arc Welding $13^{th}$ ed.," pp. 1.3-1 to 1.3.-4, 1994.

Atkins, Peter, "Physical Chemistry, $5^{th}$ ed.," W.H. Freeman & Co., pp. 400-402, 1994.

Nishikawa, K., "Plasma Physics: Basic Theory with Fusion Applications," Spring-Verlay, pp. V-XIII, 1-55, 1994.

Goldston, Robert J., et al., *Intro to Plasma Physics*, Institute of Physics Publishing, pp. 132-135, 1995.

Ellman Surgitron FFPF & Surgitron Operating Manual, pp. 1-10 (no date).

Dull, Charles E., et al., "Modern Physics," Henry Holt & Co., pp. 526-541, 1960.

Newman, James R., ed., "The Harper Encyclopedia of Science," Harper & Row Publishers, pp. 923-924, 1967.

Newman, James R., ed., "The Harper Encyclopedia of Science," Harper & Row Publishers, p. 697, 1967.

Milner, D.R. et al., "Introduction to Welding and Brazing," Pergamon Press, pp. 64-83, 1968.

* cited by examiner

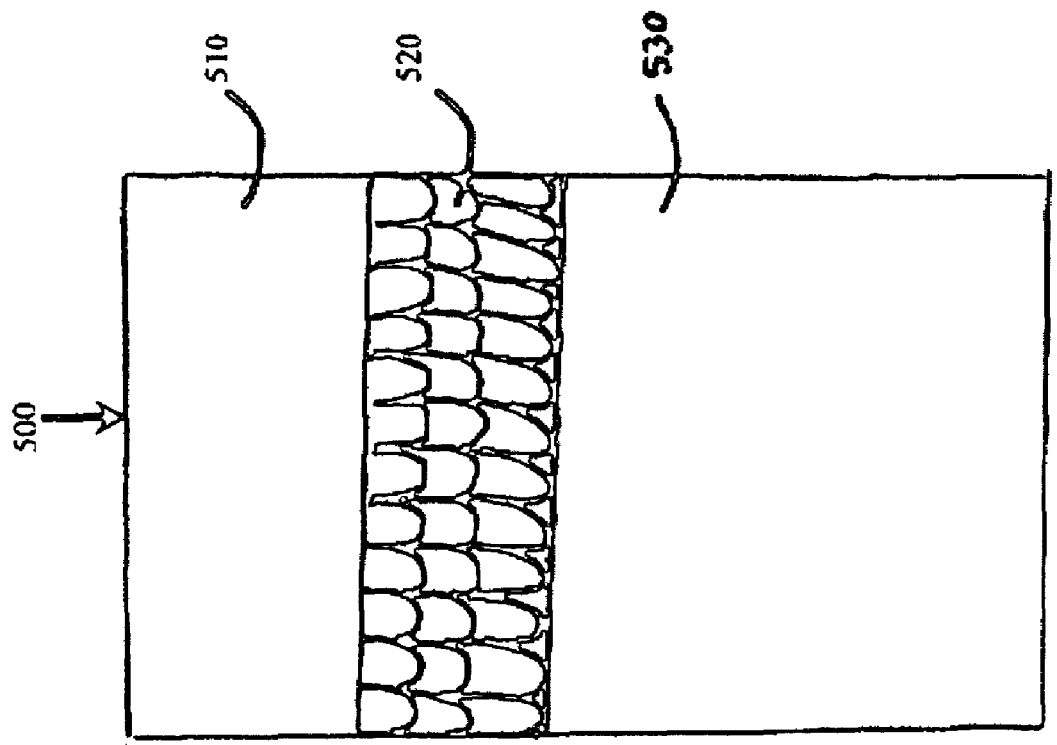
FIGURE 4-(b)
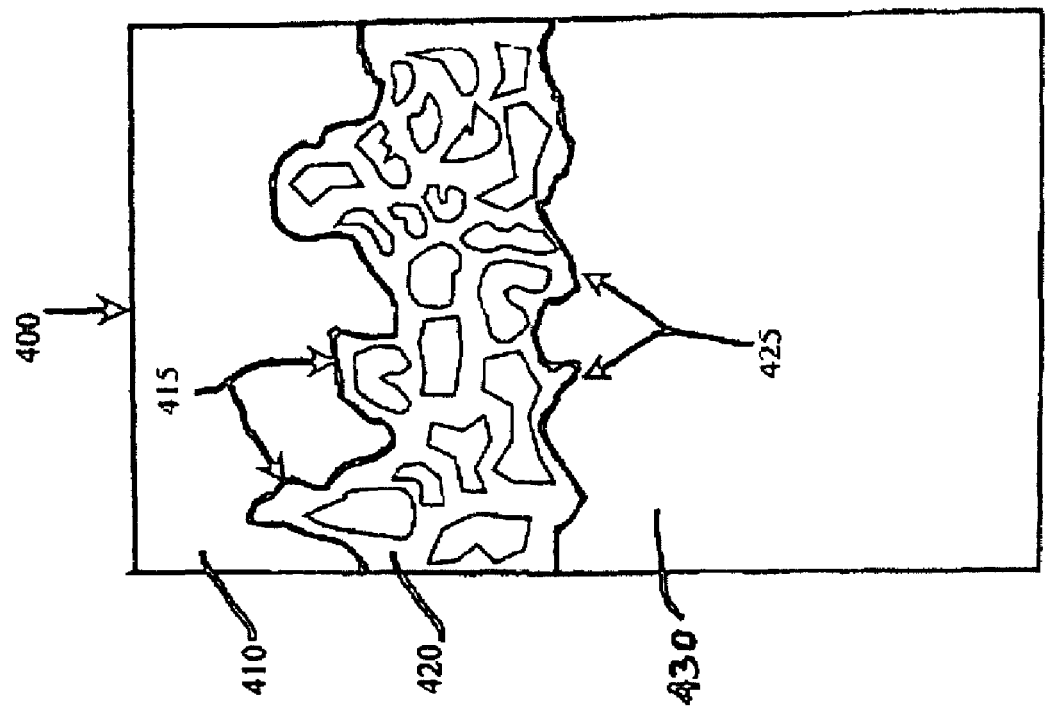
FIGURE 4-(a)

METHOD AND APPARATUS FOR PLASMA INCISION OF CARDIOVASCULAR TISSUE

RELATED APPLICATIONS

This is a non-provisional application based on provisional application U.S. Ser. No. 60/838,191 to Richard Fugo, filed Aug. 17, 2006.

FIELD OF THE INVENTION

This present invention relates to a method and apparatus for incising and ablating matter using plasma, and in particular, to a method and apparatus for performing cardiovascular surgical procedures using plasma.

BACKGROUND OF THE INVENTION

U.S. Pat. Nos. 5,958,266, 6,479,785, 6,787,730 and 6,867,387 describe methods and apparatus for incising tissue using plasma, and their separate disclosures are hereby incorporated by reference into the present application. These patents disclose how to generate and maintain plasma without using a traditional gas or liquid fuel (e.g., Argon, Xenon). Instead, these patents disclose how to generate and maintain plasma using atomic particles which surround the point of incision. Several of the patents describe a handpiece 26 with an incising electrode tip 28. In operation, the handpiece is grasped by the user (i.e., surgeon), and the incising electrode tip 28 is used to create an incision in tissue.

However, the above-referenced patents do not disclose a specific device and method for operating upon cardiovascular tissue utilizing plasma. Several U.S. patents disclose devices which utilize resistive heating (i.e., diathermy) to burn biologic tissue (such as cardiovascular tissue), but all of these devices suffer from the same drawbacks: they are all high-power devices which are difficult to control, thus resulting in the burning and destruction of unintended tissue.

Lasers have also been used to burn biologic tissue. For example, the process of 'laser angioplasty' has been used to burn away plaque within an artery. However, lasers suffer from some of the same problems as resistive heating devices (i.e., they are difficult to control and often damage surrounding tissue).

U.S. Pat. No. 7,070,595 recognizes some of the problems caused by resistive heating devices, and attempts to solve these problems through the controlled regulation of radiofrequency signal (i.e., microwave) emitted from an antenna coupled to the end of a catheter. However, although such a device may present some advantages over traditional resistive heating devices, the device still requires the heating of tissue to the point of destruction. Much like resistive heating, this type of 'radiant' heating requires high power levels, is not easily controlled, and results in the burning and destruction of unintended tissue. In essence, the device described in the '595 patent works much like a microwave oven (and even operates in same frequency range as many microwave ovens: 900-2500 MHz), in that microwaves are used to heat tissue. Much like a microwave oven, the heating cannot be easily localized to a specific point within the tissue. Accordingly, the operator of such a device (e.g., surgeon) must be careful in his or her movements, so as not to destroy unintended tissue by accident.

Thus, there is presently a need for an apparatus which permits the simple and efficient incision and ablation of cardiovascular tissue using plasma.

SUMMARY OF THE INVENTION

An exemplary embodiment of the present invention comprises an apparatus including a radiofrequency signal generator, a conditioning network coupled to the output of the radiofrequency signal generator, and a catheter coupled to the conditioning network, the catheter including at least one electrode, wherein the conditioning network conditions radiofrequency energy produced by the radiofrequency signal generator to create plasma at the at least one electrode.

An exemplary embodiment of the present invention also comprises a method for performing surgery using plasma, including the steps of disposing at least one electrode of a catheter at a point of surgery, applying radiofrequency energy to the catheter to create plasma at the at least one electrode, and ablating tissue at the point of surgery utilizing the plasma.

An exemplary embodiment of the present invention also comprises a method for ablating plaque within a blood vessel using plasma, including the steps of inserting a catheter into a blood vessel, the catheter including at least one electrode, moving the catheter to a point in the blood vessel adjacent a plaque formation, supplying radiofrequency energy to the at least one electrode of the catheter to generate and sustain plasma in the space surrounding the at least one electrode, and ablating the plaque formation using the plasma surrounding the at least one electrode.

An exemplary embodiment of the present invention also comprises a method for ablating aberrant electrical conduction pathways within the heart using plasma, including the steps of inserting a catheter into the heart, the catheter including at least one electrode, supplying radiofrequency energy to the at least one electrode of the catheter to generate and sustain plasma in the space surrounding the at least one electrode, and ablating a portion of at least one aberrant electrical conduction pathway using the plasma surrounding the at least one electrode.

An exemplary embodiment of the present invention also comprises a method for ablating precise pits into the myocardium using plasma, including the steps of inserting a catheter into the myocardium, the catheter including at least one electrode, supplying radiofrequency energy to the at least one electrode of the catheter to generate and sustain plasma in the space surrounding the at least one electrode, and ablating at least one pit in the myocardium using the plasma surrounding the at least one electrode.

An exemplary embodiment of the present invention also comprises a method for treating heart failure using plasma, including the steps of inserting a catheter into the myocardium, the catheter including at least one electrode, supplying radiofrequency energy to the at least one electrode of the catheter to generate and sustain plasma in the space surrounding the at least one electrode, ablating at least one pit in the myocardium using the plasma surrounding the at least one electrode, and stimulating neovascularization in the tissue adjacent to the at least one pit.

An exemplary embodiment of the present invention also comprises a method for ablating myocardial muscle using plasma, including the steps of inserting a catheter into the heart, the catheter including at least one electrode, supplying radiofrequency energy to the at least one electrode of the catheter to generate and sustain plasma in the space surrounding the at least one electrode, and ablating myocardial muscle using the plasma surrounding the at least one electrode.

BRIEF DESCRIPTION OF THE DRAWINGS

FIG. 4(a) shows biologic tissue which has been incised using a resistive heating device.

FIG. 4(b) shows biologic tissue which has been incised using the plasma incising system of the present invention.

DETAILED DESCRIPTION

Figure 1:
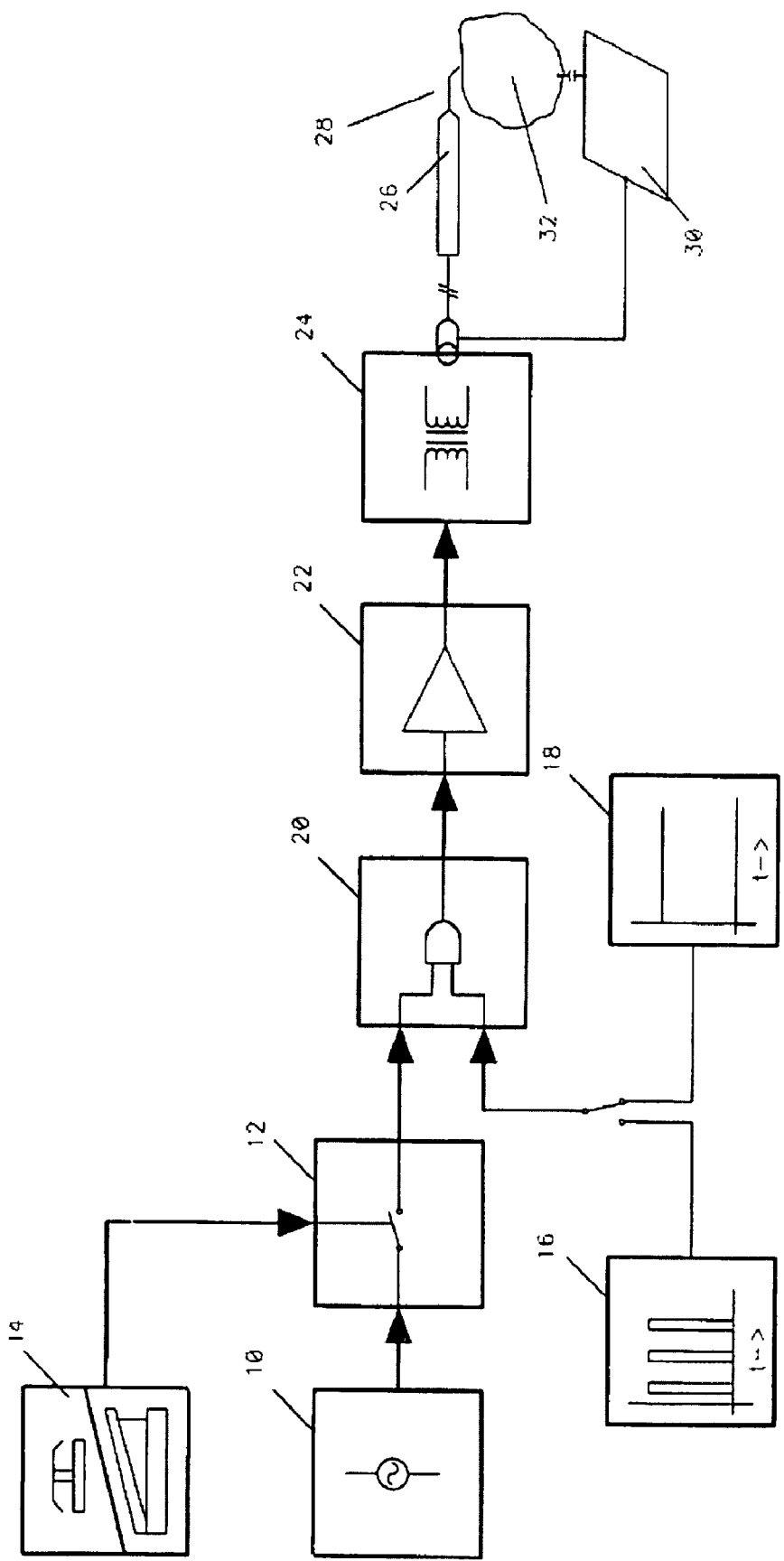
FIG. 1 is a block diagram showing a plasma incising system with resistive coupling to a patient, according to a first exemplary embodiment of the present invention.

FIG. 1 shows a plasma incising system 100 according to a first exemplary embodiment of the present invention. The system 100 includes a radiofrequency signal generator (10), a conditioning network (24), and a handpiece (26). In operation, an output signal from the radiofrequency signal generator (10) is switched on and off with a radiofrequency switch (12). The radiofrequency switch (12) is preferably coupled to an 'on-off' button or switch (14) which allows a user (e.g., surgeon) to control the application of the signal produced by the radiofrequency generator (10). The output signal from the radiofrequency signal generator (10) is preferably coupled, through a single gate (20), to either a 'burst mode' duty cycle generator (16) or a 'continuous mode' free running generator (18), depending upon the particular surgical application. The output signal from either of the 'burst mode' duty cycle generator (16) or a 'continuous mode' free running generator (18) is preferably amplified through at least one power amplifier (22). The output signal from the power amplifier (22) is then conditioned with an impedance matching and output conditioning network (24). The output signal from the conditioning network (24) is then channeled into the handpiece (26), and ultimately to an incising electrode tip (28). The incising electrode tip (28) may be applied to matter (32) to be incised through a capacitive coupling plate (30). In particular, the capacitive coupling plate (30) provides a return path for energy coupled to the matter (32) to be incised.

Figure 2:
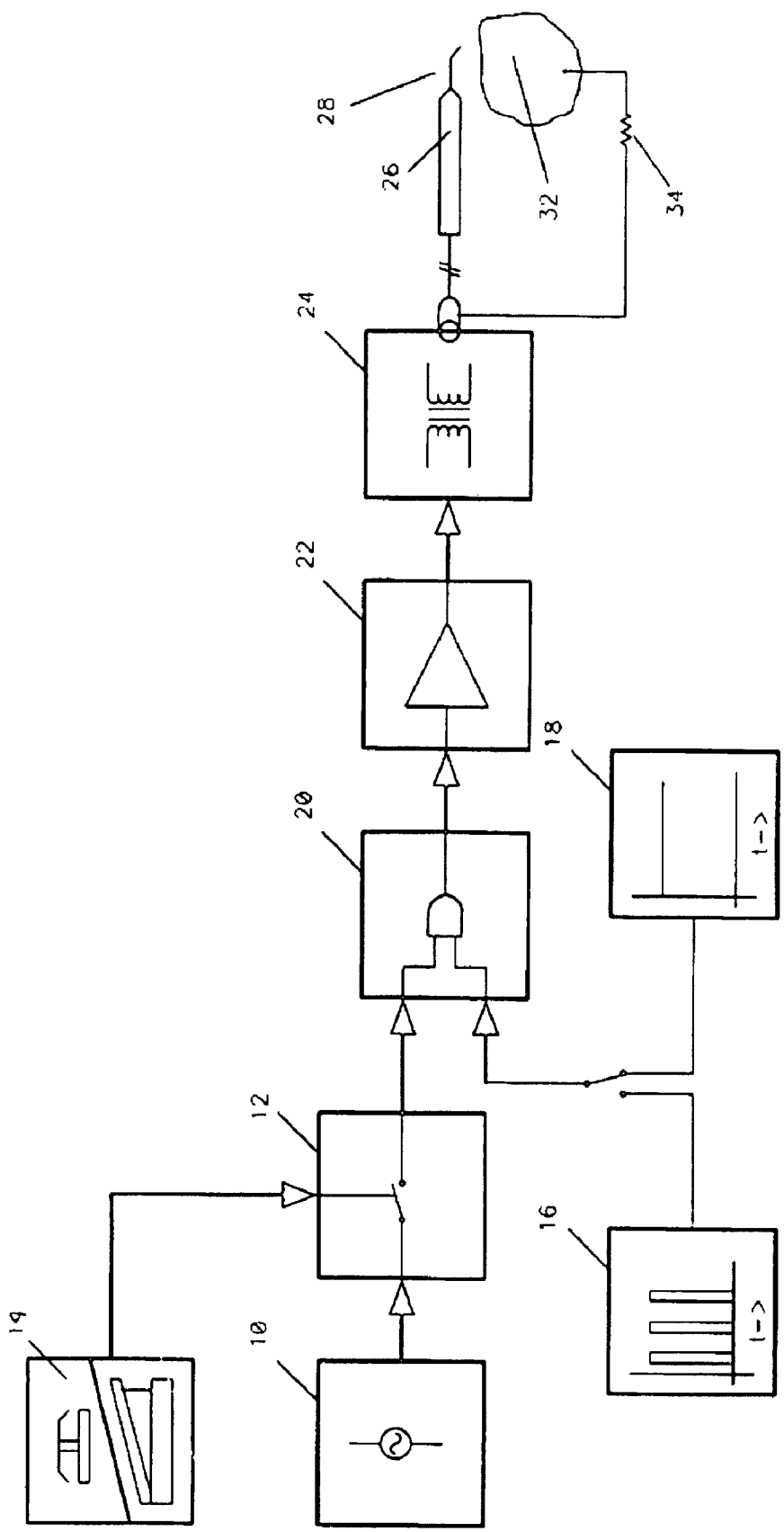
FIG. 2 is a block diagram showing a plasma incising system with capacitive coupling to a patient, according to a second exemplary embodiment of the present invention.

FIG. 2 shows a plasma incising system 200 according to a second exemplary embodiment of the present invention. The system 200 includes many of the same components and features as the system 100, and like reference numerals denote like elements. One difference between the system 200 and the system 100 is the presence of a resistive coupling electrode (34) instead of the capacitive coupling plate (30). Like the capacitive coupling plate (30), the resistive coupling electrode (34) provides a return path for energy coupled to the matter (32) to be incised. Those of ordinary skill in the art may choose to utilize the system 200 with resistive coupling under various clinical situations (such as, for example, when a surgeon desires to limit energy flow to specific portions of the body).

When the radiofrequency signal from the radiofrequency signal generator is activated (i.e., coupled to the rest of the system using the switch (12)) and the incising electrode tip is brought in close proximity to matter (32), the incising electrode tip (28) at the extreme end of the handpiece (26) becomes coated with a plasma cloud which is used to place an incision into the matter (32). As noted above, the matter (32) to be incised may be coupled to the system 100 (200) either by a capacitive coupling plate (30) (See FIG. 1), or a resistive coupling electrode (34) (See FIG. 2). The plasma cloud that coats the end of the incising electrode tip (28) reacts with atoms and molecules of matter (32) to sustain the plasma cloud.

In the above-referenced systems 100 and 200, the incising electrode tip (28) is preferably a solid, non-hollow conductor. However, partial or completely hollow incising electrode tips may be utilized without departing from the scope of the present invention. Additionally, incising electrode tip (28) is preferably linear or curvilinear in design. However, the incising electrode tip (28) may be of any shape (e.g., loop or polygon) without departing from the scope of the present invention. The systems 100, 200 are preferably utilized in the treatment of cardiovascular conditions, such as ventricular tachycardia, atrial tachycardia, and atrial flutter (fibrillation), however the systems may also be utilized in the ablation of aberrant electrical conduction pathways inside the heart.

Figure 3:
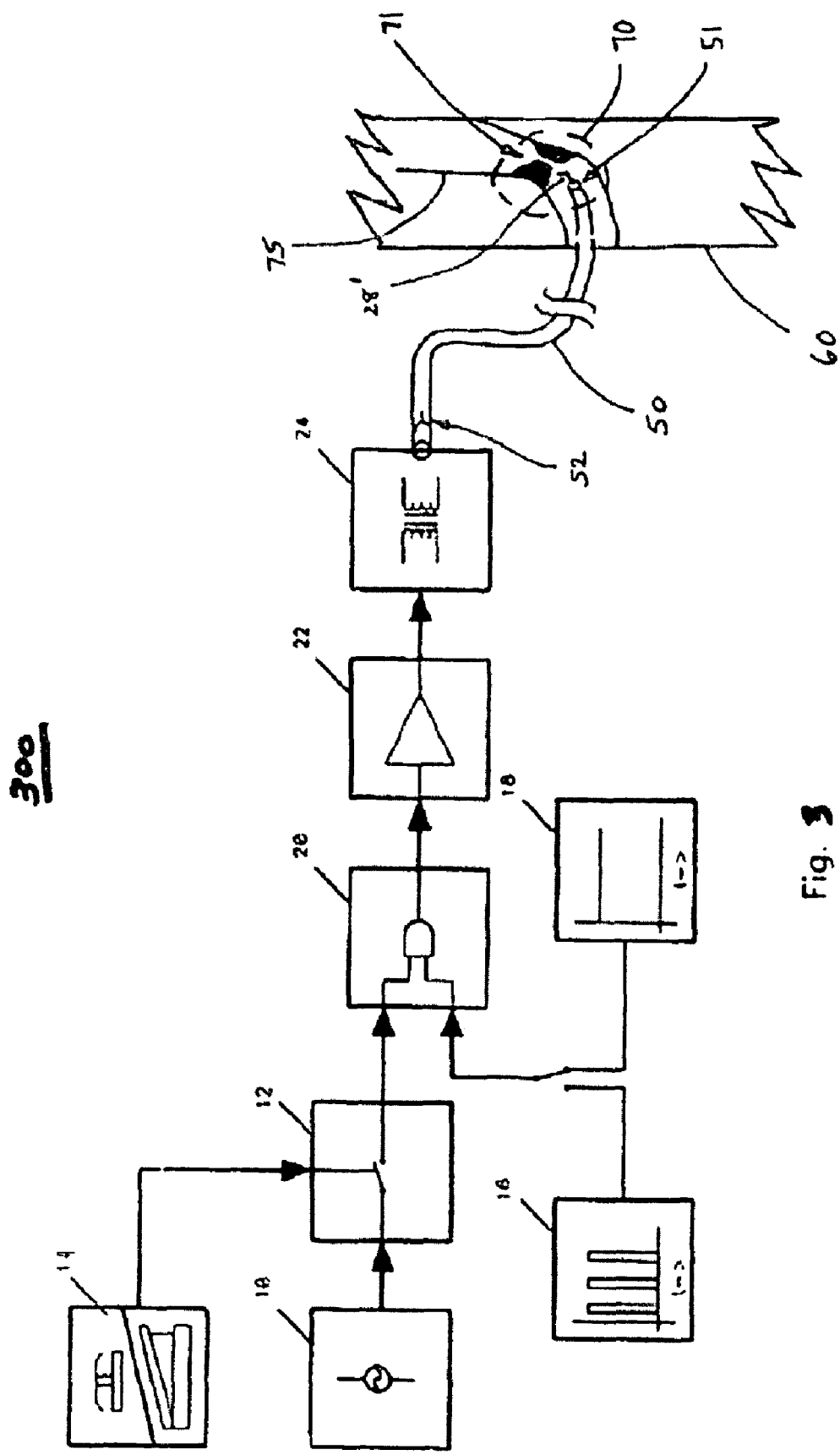
FIG. 3 is a block diagram showing a plasma incising system including a catheter for insertion into a patient, according to a third exemplary embodiment of the present invention

FIG. 3 shows a plasma incising system 300 according to a third exemplary embodiment of the present invention. The system 300 includes many of the same components and features as the systems 100 and 200, and like reference numerals denote like elements. However, the system 300 does not include a handpiece, but rather includes a catheter or operating "scope" for small incision surgery (50) coupled directly to the conditioning network (24) at a proximal end (52). As shown in FIG. 3, the distal end (51) of the catheter (50) may be inserted into biologic tissue (60) (e.g., human tissue), and routed through known methods to a point of surgery 70 (e.g., a clogged vein or artery). The distal end (51) of the catheter (50) includes an incising electrode tip (28') which is similar in operation to the incising electrode tip (28) discussed above. In particular, the incising electrode tip (28') generates plasma that surrounds and coats the incising electrode tip. This plasma may be used to ablate, eliminate or destroy tissue at the point of surgery (70), such as for example, plaque (71) which has formed within an artery (75). In addition to the incising electrode tip (28'), the catheter (50) may also include one or more optic fibers for illumination and image capture, and/or an irrigation/aspiration cannula.

As noted above, the catheter (50) of the system 300 may be used in cardiovascular surgery to treat conditions such as atherosclerosis and coronary thrombosis (i.e., clogged arteries) by destroying or ablating (with plasma) the plaque formation which is causing the blockage. The catheter (50) may also be utilized in a variety of other cardiovascular procedures. For example, the catheter (50) may be used to treat conditions such as ventricular tachycardia, atrial tachycardia, and atrial flutter (fibrillation), by allowing the plasma ablation or destruction of damaged tissue within the heart which causes such conditions. The ablation of aberrant electrical conduction pathways of the heart may also be accomplished using the system 300 of the present invention.

Although the above-referenced cardiovascular procedures may be performed with existing electrosurgical devices, such as resistive heating (i.e., diathermy) devices, these devices all suffer from control problems which necessarily result in unwanted damage to adjacent vital tissue. Histologic studies have demonstrated the precision and high control of the present invention over standard diathermy devices (See, FIGS. 4(a) & 4(b)). Thus, the systems 100-300 according to the present invention are not only efficacious, but much more controlled than existing diathermy devices. Using the systems 100-300 of the present invention, a user (e.g., surgeon) is able to remove unwanted tissue without damage to adjacent tissue and structures.

In the specific cases of heart failure and myocardial ischemia, existing diathermy and laser devices may be used to place pits into damaged sections of heart muscle. However, these devices suffer from control problems which necessarily result in unwanted damage to vital tissue adjacent to the myocardial pit. Likewise, these devices have difficulty in achieving precise pit depth into myocardial tissue. The systems 100-300 of the present invention allow the user to place a precise ablation pit into the myocardium which avoids unwanted damage to adjacent vital tissue. The superficial inflammation produced by the systems 100-300 of the present invention may also precipitate a desirable angioneoginesis/neovascularization (growth of new blood vessels) at the pit interface, and thereby promote blood flow with increased oxygen supply for the myocardial tissue. These same 'clean' ablation pits in myocardium are ideal receptacles for the injection of stem cells. These stem cells may release cytokines, growth factor, anti-apoptotic molecules, etc. which serve to reinforce and strengthen the cytoskeleton of the heart. Stem cells may also transform into functional myocardial muscles thereby replacing damaged heart tissue.

Furthermore, plasma ablation with the systems 100-300 has minimal effect on triggering myocardial contraction. Accordingly, heart tissue undergoing ablation manifests minimal irregular contraction or fasciculation even when this tissue is hypoxic (which usually makes the cells hypersensitive to stimuli). This quality provides surgeons with a great opportunity to manipulate heart tissue, replace heart tissue, and/or reconstruct cardiac structures (such as, for example, in cardiac valve alteration or replacement).

In all of the systems 100-300 described above, the output of the system (i.e., a conditioned electromagnetic waveform) is preferably impedance matched, frequency matched, power matched and 'Q' curve matched (and thereby tuned) to the plasma cloud and the matter surrounding the incising electrode tip (28, 28') to create a controlled and harmonious plasma cloud at the tip which may used for incising or ablating matter (e.g., biologic tissue, plant tissue, etc.). The production of a harmonious plasma around the incising electrode tip (28, 28') results in a visible, organized plasma cloud which may be easily and efficiently initiated, sustained and modified. It should be noted that, as explained in detail below, the harmonious plasma cloud is only created when the incising electrode tip (28, 28') is brought in close proximity to the matter being incised (e.g., within 50-10,000 microns). This is because the particles of matter are utilized as the primary fuel for sustaining the plasma, which in turn forms a primary plasma cloud. Additionally, as those particles are used in the plasma cloud to incise or ablate tissue (and eventually expelled from the plasma cloud), new particles from the matter are drawn in to the plasma cloud, thus creating a harmonious and sustained plasma suitable for incising and ablating matter. This 'vacuum effect' for the particles of matter entering and exiting the plasma cloud is discussed below. The harmonious plasma cloud coating the incising electrode tip (28, 28') also manifests substantially reduced atomic particle chaos and turbulence (inside the plasma cloud) as compared to existing plasma cutting systems.

In particular, the incising electrode tip (28, 28') emits an empirically conditioned electromagnetic (EM) waveform that is specifically tuned to the plasma cloud and the matter incised, such that the EM field is highly absorbed by the molecular lattice of matter which is in contact with the tip, thereby causing the molecules to absorb the EM wave energy and thereby raise the molecular bond energy to the point where bonds fracture. These fractured molecular particles are then transformed into plasma. As noted above, this EM wave is empirically tuned to the plasma cloud and the specific matter surrounding the incising electrode tip (28, 28') so that the EM wave is frequency matched, impedance matched, power matched, and Q curve matched to the plasma cloud and the matter. This empirical matching results in a plasma cloud that forms a thin coat around the incising electrode tip (28, 28'), and manifests a controlled, orderly character which may be termed "harmonious plasma." "Harmonious plasma" as described herein is a specific form of plasma that manifests a highly controlled, non-caustic character when existing in specific environments. "Harmonious plasma" is based upon specific physical parameters such as plasma electron density, plasma electron oscillation frequency, plasma electron kinetic energy, plasma ion density, plasma ion oscillation frequency, plasma ion kinetic energy, etc.

In all of systems 100-300, atoms from the fractured molecular lattice of the matter being incised are extracted from the lattice (matter) and into the harmonious plasma cloud where they exist for a short interval. In this manner, the systems 100-300 act as "micro-vacuum cleaners" which continuously pull more fractured atoms generated by the conditioned EM wave energy into the plasma pool while also continuously discharging energy depleted atomic particles which have been present previously. Therefore, there is a constant stream of atoms extracted from the molecular lattice (of the matter) by the incising electrode tip (28, 28'). Because the constant flow of atoms from the fractured molecular lattice (matter) serves as fuel for the harmonious plasma cloud, traditional plasma fuels (e.g., Noble gases such as Argon, Xenon, etc.) are not necessary. Additionally, plasma devices which are 'gas-fueled' generate significant heat which necessarily cause burning of tissue. In this way, gas-fueled plasma devices are analogous to a cigarette lighter which uses burning gas (e.g., butane) to create a flame in order to ignite or oxidize matter. The systems 100-300 of the present invention exhibit very little (if any) burning or oxidizing of matter, as shown by histologic studies (See FIGS. 4(*a*) & 4(*b*)).

The harmonious nature of the plasma cloud produced by the systems 100-300 also allows an increased concentration of energy in the intended path of incision, with less energy spillover outside of the intended path of incision. Thereby, the above-described systems 100-300 are able to achieve a cleaner, more precise, more powerful and more efficient incision with less impact on matter outside of the intended path of incision than existing systems which rely on resistive heating, laser heating or microwave heating of tissue.

FIG. 4(*a*) of the present application shows an incision made in biologic tissue 400 using a standard resistive heating (e.g., diathermy) device, and FIG. 4(*b*) shows an incision made in biologic tissue 500 using a plasma incising system according to the present invention (e.g., one of systems 100-300). As will be seen when comparing the figures, the tissue 400 incised with a resistive heating device has an incision wall 420 which exhibits large irregularities 415, 425 over the surface of the incision wall 420, particularly on a side of the incision wall adjacent a tissue surface 410, and on an exterior side 430. These irregularities 415, 425 result from the burning of tissue in an uncontrolled manner (which also results in scarring of the same tissue), as is the case with resistive heating devices, microwave heating devices, and certain types of lasers. Such irregularities also exist within the tissue of the incision wall 420, as also shown on FIG. 4(*a*). Alternatively, when biologic tissue 500 is incised or ablated using the present invention, the incision wall 520 is virtually free of irregularities (and actually exhibits a regular and defined pattern within the tissue), and so are the sides of the incision wall which face the tissue surface 510 and the exterior surface 530, as shown in FIG. 4(*b*). The ability to create these 'clean' incision walls sets the present invention apart from existing heating devices (and lasers) which, as noted above, burn and scar the tissue being incised.

The systems 100-300 all employ an inexpensive, electronic radiofrequency generator (10) and conditioning network (24)

to produce, condition and transmit a continuous or pulsed electromagnetic field from an incising electrode tip (28, 28'). The radiofrequency generator (10) may generate signals with a frequency of up to 500 MHz (depending upon the characteristics of the matter to be ablated or incised), but preferably generates signals with a frequency in the Very Low Frequency (VLF) band (e.g., 9-15 MHz), which results in an electromagnetic field in the same frequency range. Alternatively, existing microwave heating devices operate in a frequency band much higher than the present invention (e.g., 900-2500 MHz (0.9-2.5 GHz)), and in the preferred embodiment described above, over one hundred (100) times higher. That is not to say that the systems 100-300 cannot operate effectively in higher frequency ranges (e.g., greater than 50 MHz) in certain situations, however, the VLF band is suitable for many incising and ablating applications. The cycle time of the electromagnetic field in 'pulsed' mode is variable, and each complete on-off cycle of the pulsed mode may be as short as 0.000001 second (i.e., one 1 microsecond (µs)). Specific parameters of the systems 100-300 are largely determined by the atomic particle composition along the interface of the incising electrode tip (28, 28'), and the matter (32, 60) into which an incision is placed. This is because the systems 100-300 all utilize atoms along the interface of the incising electrode tip (28, 28') and the matter (32, 60) into which an incision is placed to generate and sustain the harmonious plasma cloud. This is as opposed to existing systems which require that an ionizable gas (e.g., Argon) be injected into the field of incision to create and sustain plasma. Although the systems 100-300 may utilize ionizable gases as supplementary fuel for the plasma, they are not required.

The EM wave created by the systems 100-300 is a form of radiant electromagnetic energy and is transmitted outward from the incising electrode tip (28, 28'). The radiant electromagnetic energy is specifically conditioned to interact with atoms and molecules at the surface of the incising electrode tip (28, 28'). Electromagnetic frequencies secondarily produced from atomic particle interaction and dynamics at the incising electrode tip (28, 28') play a substantial role in the system function and effectiveness. Harmonic frequencies of the fundamental generated electromagnetic waveform often play a substantial role in system function, dynamics and effectiveness. The radiant electromagnetic energy interaction with atoms and molecules includes thermal ionization and the photoelectric effect which strip electrons from the atomic orbitals of atoms at the interface of the matter (32, 60) and the incising electrode tip (28, 28'). Such processes result in atomic transformation of atoms and molecules into ions and free electrons. The free charged atomic particles move through space before colliding with electrons of other electrode interface atoms thereby knocking more electrons out of their atomic orbitals. Repeating this process produces a chain reaction of charged atomic particle collision known as the Avalanche Effect which thereby participates in the formation of a cloud of plasma at the surface of the incising electrode tip (28, 28').

As noted above, the EM waves output by all the systems 100-300 are impedance matched, frequency matched, power matched and tuned to the molecular lattice of the matter being incised and the plasma cloud coating the incising electrode tip (28, 28'). As noted above, the plasma cloud does not exist in a stable state until the incising electrode tip (28, 28') is brought in close proximity to the matter being incised or ablated because the systems have been previously matched and tuned to the matter. The systems 100-300 all condition the electromagnetic waveform provided at the incising electrode tip to provide a tightly coupled, highly efficient energy transfer to the molecular lattice of the matter being incised and the plasma cloud, in order to allow maximum energy transfer from the incising electrode tip (28, 28') into the molecular lattice of the matter and the plasma cloud with minimal loss of electromagnetic radiant energy into the matter surrounding the intended path of incision. Physical chemistry principles are employed to control the shape and characteristics of the plasma cloud including the regulation of atomic particle chaos in the plasma cloud. In this way, the systems 100-300 all produce a harmonious, controlled plasma that focuses energy into the intended path of incision as opposed to the caustic, disharmonious plasma 'arcing' seen in existing electrosurgical units. The harmonious plasma cloud produced by the present invention possesses lower atomic particle chaos and turbulence than existing electrosurgical systems, thereby producing a more efficient incision into matter.

Arcing is a form of disharmonious plasma flow and represents uncontrolled, turbulent flow of ionized atomic particles in plasma, thereby producing increased atomic particle chaos and turbulence in the plasma. Merely reducing the cutting tip power does not in itself significantly improve the plasma harmony in as much as it does not greatly decrease the flow turbulence or flow chaos of the ionized atomic particles that make up a plasma arc. As with other forms of matter, plasma has a wide range of physical presentation including a wide range of temperature, density, flow characteristics, atomic particle components, etc. On earth, plasma arcing can be found in a number of areas such as welding arcs, spark plug arcs, lightning bolt arcs, neon lights and electro-cutting or electrosurgical arcs. The substantial intensity of atomic particle turbulence in classic electrosurgical plasma arcs represents a form of elevated atomic particle chaos, wherein the uncontrolled nature of the atomic particle chaos is caused by turbulent flow of the atomic particles in the plasma cloud. This form of plasma represents disharmonious plasma and when used for cutting results in substantial heating and/or a significant quantity of energy spillover into matter outside of the intended path of incision. This energy spillover extending beyond the intended path of incision into matter results in energy exposure, thermal exposure and damage to surrounding matter. The present invention minimizes plasma arcing by substantially reducing the atomic particle turbulence and chaos in the plasma cloud, thereby generating a harmonious plasma cloud.

As the electromagnetic field traverses the thin coating of harmonious plasma surrounding the incising electrode tip (28, 28'), the electromagnetic field is slowly damped or decreased in amplitude. Finally, the electromagnetic field will pass substantially through the plasma cloud and will encounter matter outside of the intended incision path, namely the matter (32, 60) which surrounds the plasma cloud. According to the physical chemistry principle of Tunnelling, the generated electromagnetic wave then encounters a barrier to which it is not tuned nor impedance matched and thereby a substantial percentage of the remaining energy of the electromagnetic wave is reflected back into the harmonious plasma cloud. This reflected electromagnetic energy acts to further energize the molecular particles in the plasma cloud, thereby reducing the output energy which must be transmitted by the electromagnetic wave generator system. This process also serves to reduce the percentage of total electromagnetic radiation that penetrates into, that reacts with, and that presents potential radiation exposure damage to matter outside of the intended incision path, thus reducing damage to matter outside the incision path.

The centripetal force of the generated electromagnetic field is used to control the distance between the atomic particles in the harmonious plasma cloud. The ionized particles travel in spiral paths in magnetic fields while the individual ionized particles may simultaneously be oscillating, vibrating, spinning and/or precessing. Furthermore, the Pinch Effect of plasma physics is employed to compress, contour, shape and control the harmonious plasma cloud with a solid, hollow or semi-hollow incising electrode tip (28, 28'). The Magnetic Bottle Effect of nuclear physics, may also be employed to trap and contain the compressed plasma cloud without the need of solid matter containment vessels, and thereby avoid the requirement to employ hollow or cavity containing incising tip probes or external magnetic arrays to trap and control the plasma cloud. Increasing the density of atomic particles in the harmonious plasma cloud allows a substantial increase in plasma cloud power density, thereby improving the cutting efficiency and the effective power of the plasma cloud.

Furthermore, compressing the plasma cloud causes a substantial decrease in the cross sectional diameter of the plasma cloud thereby decreasing the width of the intended incision path, as well as minimizing side effects or potential adverse impact on matter outside of the intended path of incision. In particular, once the radiofrequency signal generator (10) of the systems 100-300 is powered 'off,' the energy level of the harmonious plasma cloud rapidly decays to a point at which the atomic particles comprising the plasma cloud cannot be sustained in the state of matter known as plasma. When the particle energy level falls below a given threshold, the lower energy particles revert to a solid or semisolid physical state. In essence this means that the systems 100-300 are extremely precise, and do not experience a substantial 'power down' time or cycle in which the effects of the plasma are still felt on the matter (as opposed to diathermy units which experience a 'cooling off' period after operation in which heating of tissue continues to occur).

Accordingly, the systems 100-300 of the present invention all employ a specifically tuned electromagnetic wave to generate a harmonious plasma which may have its shape, contour, power density and physical characteristics controlled to allow the production of a more efficient, more controlled, less toxic and more cost effective method of incising matter using plasma. The systems 100-300 of the present invention do not oxidize, burn or otherwise char tissue in order to accomplish destruction or ablation, as opposed to existing electrosurgical devices (e.g., resistive heating devices, microwave heating devices) which burn or oxidize tissue in order to destroy or ablate it.

Again, whereas existing electrosurgical units employ inefficient, poorly controlled and caustic ohmic diathermy (i.e., resistive heating and burning of tissue) to produce an incision into matter, the system according to the present invention utilizes conditioned, transmitted power to create and sustain a thin cloud of harmonious plasma which coats an incising electrode tip. Thereby, a more efficient utilization of energy is implemented with the present invention than in existing electrosurgical systems. In sum, the present invention permits the creation of an incision in matter without significant heating or burning by utilizing the energy of a controlled, harmonious cloud of plasma atomic particles surrounding an incising electrode tip. Furthermore, the systems 100-300 according to the exemplary embodiments of the present invention have the following advantages:

(1) they permit an inexpensive production of plasma;
(2) they permit an efficient production of plasma;
(3) they permit a controllable production of plasma;
(4) they permit the production of a plasma which may place an incision into solid matter;
(5) they employ known physical principles to maximize transfer of radiant electromagnetic energy into the molecular lattice of an intended path of incision and thereby to generate a harmonious plasma;
(6) they employ known scientific principles to allow radiant electromagnetic energy to interact with, stimulate, and energize atomic particles which themselves may be oscillating, vibrating, spinning, and/or precessing.
(7) they provide the production of a plasma with lower atomic particle chaos and lower atomic particle turbulence than produced with classic plasma cutting devices, thereby allowing the production of a harmonious plasma;
(8) they produce an incision into matter with a thinner corridor of matter involved in the path of incision;
(9) they produce an incision into matter which utilizes the Tunnelling Effect of physical chemistry to shield matter outside of the intended path of incision from electromagnetic radiation, thereby reducing the need to employ shields constructed of various forms of matter;
(10) they utilize a centripetal electric field force and a magnetic field force to trap the created plasma around the incising electrode tip;
(11) they utilize the Pinch Effect to compress, contour and control both the shape and density of the plasma cloud, thereby eliminating the need for bulky containment chambers to encase the generated plasma;
(12) they eliminate the need for substantially complicated designs for transmitter incising electrode tips;
(13) they eliminate the need for elaborate plasma control devices or chambers such as a tokamak or cyclotron;
(14) they produce an incision into matter which is inexpensive, clean, efficient, safe and controllable;
(15) they produce an incision into vascular tissue that produces a non cauterizing hemostasis known as "autostasis";
(16) they produce an incision into matter that kills microbes, thereby creating an incision that also produces bacterial decontamination of the incision site;
(17) they produce an incision into matter that fractures toxic substances such as mustard gas, thereby decontaminating the incision site from toxic chemicals;
(18) they produce an incision into matter that removes unwanted surface debris from the area of the intended path of incision, thereby creating a surface ablation which can remove surface abnormalities such as skin wrinkles, skin pathology as well as unwanted foreign matter from the surface of the ablation site; and,
(19) they produce incision walls that are so clean that minimal necrotic debris must be removed by the body from the plasma ablation incision before the body healing process commences thereby producing a clinical situation where there is less swelling, less inflammation, less pain and a reduced healing time.

In sum, the systems 100-300 according to the exemplary embodiments of the present invention all involve impedance matching, power matching, frequency matching, Q curve matching (and thereby tuning) the output of the systems (i.e., the EM wave) to the unrefined plasma cloud surrounding the incising electrode tip (28, 28') and the matter being incised to create and sustain a controlled and harmonious plasma at the incising electrode tip. This matching transforms the unrefined plasma cloud into a refined and harmonious plasma cloud, and (as discussed above) allows matter in the path of the incision to absorb EM field energy in a highly efficient manner. For example, too little system power will cause extinguishment of the plasma cloud, whereas too much system power will cause the plasma cloud to loose its harmonious character, and thus become explosive and uncontrolled. As the appropriate system parameters are approached, the system power requirements will decrease while the integrity of the harmonious plasma cloud increases. The refined harmonious plasma cloud may be observed both electronically and visually (e.g. through a high resolution microscope).

As discussed above, the plasma incising systems 100-300 described above may be utilized for performing surgical procedures on cardiovascular tissue, that is, tissue that comprises the heart and the blood vessels (e.g., veins, arteries, and capillaries) of the human body. The plasma incising systems 100-300 may also be utilized for performing surgical procedures on lymphatic tissue, which is a very important component of the overall cardiovascular system. For certain cardiovascular procedures, system 300 is preferable because it permits direct access to the heart and blood vessels without a large incision.

The use of the present plasma incising systems 100-300 in the above-referenced procedures allows cardiovascular and lymphatic tissue to be ablated (i.e., completely removed) in a safe, controlled, fashion that reduces tissue damage, that contemporaneously sterilizes the area of incision, and that minimizes unwanted bleeding. The plasma incising systems 100-300 may operate on very little power (e.g., battery power), and are also portable, which allows them to be used in a variety of environments (i.e., environments where electrical power is not readily available, such as in battlefield situations).

Some objectives of the present invention include (but are not limited to): (1) enhancing cardiovascular surgery by providing discreet and controlled ablation of cardiovascular tissue, and (2) enhancing general thoracic surgery by providing a highly-controlled ablation of thoracic structures, including but not limited to, the heart, lung, esophagus, thoracic wall, ribs, autonomic nerve chain, diaphragm, and great vessels including the aorta and its branches.

Histologic studies have demonstrated that no significant cauterization of an incision wall occurs during ablation with the present invention, yet it also produces a novel non-cauterizing hemostasis known as "autostasis". However, the device tuning may be adjusted so that the production of coagulation/cautery of the incision wall may be increased if so desired by a surgeon for a given maneuver. Moreover, clinical observation has demonstrated that ablation with the present invention significantly reduces bleeding, thereby improving visualization of the surgical site by the surgeon, and improving the safety of surgery and limits blood loss from the patient, as well as reducing surgical time. In this regard, the present invention provides many advantages over existing electro-optical, and electrosurgical systems, which removing tissue by heating or burning processes (i.e., diathermy, microwave heating, laser).

With regard to cardiovascular surgery, the present invention allows the ablation of electrical conductive pathways through large incision access or small incision access. In particular, the present invention may be used to ablate electrical conductive pathways for such pathology as ventricular tachycardia, atrial fibrillation, and in cases of cardiovascular 'aberrant' pathways. Specifically, the present invention may be used to ablate electrical pathways within the heart which are either not working properly, or are leading to the wrong locations within the heart (i.e., aberrant). The present invention may be used to ablate these 'aberrant' pathways, and thus correct conditions such as irregular heartbeats which may be life threatening. The present invention also enhances the effectiveness of cardiovascular reconstructive surgery by providing a more controlled, and less caustic, method for performing delicate procedures such as heart valve reconstruction or replacement.

The present invention also allows for improvements in the treatment of heart failure by permitting the creation of controlled channels into the myocardium. The creation of controlled channels in the myocardium, in turn, produces a highly localized inflammation immediately along the walls of the ablation path, thereby stimulating blood vessel angiogenesis, which increases oxygen for the myocardial tissue. This procedure can further be augmented by adding stem cells into the plasma ablation channels wherein these stem cells in turn generate chemicals such as cytokines, growth factors and anti-apoptotic molecules into the myocardium in order to strengthen the cytoskeleton of the heart. Stem cells may transform and reorganize into functional myocardial muscle fibers thereby replacing damaged heart muscle. Furthermore, the present invention has minimal effect on triggering myocardial fasciculation or inappropriate contraction, and thus, heart tissue undergoing ablation with the present invention shows minimal irregular heart contraction or heart fasciculation even when this tissue is hypoxic. Hypoxic heart tissue is often hypersensitive to external stimulation, and the present invention allows the surgeon to manipulate such heart tissue, and/or to replace or reconstruct heart structures, such as in heart valve reconstruction or replacement.

The present invention also permits the rapid and safe ablation of blood vessel plaque formation, either in a large open incision, or through use of a catheter. If a catheter is utilized, it may be guided through a small skin perforation, into a blood vessel, and through the vessel to a point or zone of plaque blockage. Plasma can then be created at the exact point or zone to effectively ablate the plaque formation, thereby opening closed vessels. The ability to generate controlled plasma on the tip of a catheter or "invasive scope" provides the capability to perform minimally invasive cardiothoracic surgery in a safer, quicker, more controlled manner employing much more cost effective and rugged equipment than has been utilized previously. This safe and efficacious procedure can provide blood vessel patency without the need to surgically open the chest, thereby eliminating a substantial percentage of open heart surgeries.

Because of the minimally invasive nature of the present invention, many cardiovascular procedures may be easily and efficiently performed including repair, removal and/or replacement of damaged heart and blood vessel tissue (which may be combined with reparative devices, such as prosthesis or stem cells). This also allows for atraumatic ablation of cardiac vegetations and ectopic tissue, as well as providing the capability to reorganize or reconfigure cardiac tissue in order to improve patient health.

With regard to general thoracic surgery (as with cardiovascular surgery discussed above), the present invention allows large incision or catheter based ablation which is minimally invasive, and safer, quicker, more controlled and less expensive than existing methods for all structures that compose the thoracic cavity.

Although the plasma systems 100-300 described above may be used to ablate many different types of matter, the following two (2) embodiments comprise preferred parameters for the ablation of cardiovascular tissue (e.g., heart tissue, vessel plaque formations, etc.). Those of ordinary skill in the art will understand that these embodiments are only exemplary, and various other embodiments (and sets of parameters) are within the scope of the present invention.

Embodiment 1 is intended for use in incising lighter tissue, and Embodiment 2 is intended for use in incising thicker or heavier tissue.

| Embodiment 1 | |
| --- | --- |
| Output Voltage (Vp-p) | 180-230 Volts |
| Output Frequency | 9.8-9.9 MHz |
| Pulsed Peak Output Power | 9.0-14.7 Watts Peak RMS |
| Average Output Power | 0.40-1.82 Watts |
| Duty Cycle | 4.48-12.37% (on time) |
| Total Burst Cycle Time | 20.5-24.5 milliseconds (ms) |
| Burst 'On' Time | 0.92-3.03 ms |
| Output Impedance | 400-600 Ohms |
| Burst Modulation | Square Wave |
| Carrier Modulation | Sine Wave |
| Incising Electrode Tip Material | #304 Stainless Steel |
| Incising Electrode Tip Shape | Solid tubular |
| Incising Electrode Tip Dimensions | 0.75 millimeters (mm) × 100 microns (μm) |

| Embodiment 2 | |
| --- | --- |
| Output Voltage (Vp-p) | 900 Volts |
| Output Frequency | 13.5-13.6 MHz |
| Pulsed Peak Output Power | 200-300 Watts Peak RMS |
| Average Output Power | 20-30 Watts |
| Duty Cycle | 0.10-10% (on time) |
| Total Burst Cycle Time | 5-10 milliseconds (ms) |
| Burst 'On' Time | 0.005-10 ms |
| Output Impedance | 300-600 Ohms |
| Burst Modulation | Square Wave |
| Carrier Modulation | Sine Wave |
| Incising Electrode Tip Material | #304 Stainless Steel or medical grade Tungsten |
| Incising Electrode Tip Shape | Polyhedron; rectangular parallelepiped |
| Incising Electrode Tip Dimensions | 2.0 centimeters (cm) × 0.5 cm × 2.0 millimeters (mm) |

As will be noted from an examination of the above parameters, the systems 100-300 of the present invention operate on very little output power (1-2 Watts) as compared to existing resistive heating devices, and existing microwave heating devices, which require at least 50 Watts of output power to effectively destroy tissue. Particularly, the systems 100-300 can operate from battery power alone. Additionally, the systems 100-300 of the present invention operate in a completely different frequency band (9-10 MHz—Very Low Frequency—VLF) as compared to existing microwave heating devices, which operate in traditional microwave heating bands, such as 900-2500 MHz (0.9-2.5 GHz). Thus, whereas existing electrosurgical systems operate on a 'high power-high frequency' concept, the present invention operates on a 'low power-low frequency' concept which allows for a significant reduction in the destruction of tissue surrounding the point of incision or surgery. Additionally, the systems 100-300 of the present invention operates at frequencies much lower than electro-optical devices (e.g., lasers). Furthermore, the systems of the present invention are much more precise than lasers and microwave heating devices. In particular, lasers produce linear streams of photons that have a high risk of damaging vital tissue by unwanted penetration of vital tissue (such as the unwanted creation of a hole through a coronary artery). Likewise, microwave heating systems produce complex EM transmission waveforms which make it difficult to precisely focus energy. This lack of focus results in a high risk of destroying adjacent vital tissue, much as would be the case if a microwave oven lacked a shield along its walls to stop the microwave energy from transmitting outside of the oven.

Although exemplary embodiments of the present invention have been described above for use in procedures involving cardiovascular tissue, those of ordinary skill in the art will realize that the systems 100-300 of the present invention may be used for other incising and/or ablating many other types of tissue. For example, the systems 100-300 may be used:

(1) to enhance general abdominal surgery by providing a highly controlled ablation of abdominal structures including organs, blood and lymph vessels, nervous system structures, and musculoskeletal structures;

(2) to enhance orthopedic surgery by providing a highly controlled ablation of orthopedic structures. In particular, the present invention may be used to ablate paths as narrow as ten (10) microns in bone in a resistance free fashion. The present invention provides a distinct advantage over existing orthopedic techniques, such that unwanted bone tissue may be ablated, while comminuted fractures can be treated by placing anchoring/stabilization holes through bone fragments without placing undue stress on the bone fragment. Likewise, cartilage and tendons can be more easily reshaped, repositioned or ablated;

(3) to enhance plastic and reconstructive surgery by providing a highly controlled, resistance free ablation capability. Particularly, the present invention may be used to remove unwanted surface lesions, or eliminates wrinkles by tightening upper layers of the skin. The present invention permits incisions that are as thin as five (5) microns with little to no trauma to the incision wall (as shown in FIGS. 4(a) and 4(b) of the present application), thus allowing the body to begin healing almost immediately (since there is no significant debris to remove from the incision), and significantly reducing scar tissue;

(4) to enhance all surgery in vascular tissue by reducing bleeding and simultaneously improving visualization of the surgical site. The highly controlled ablation of the present invention results in little or no bleeding at the surgical site, thus improving the safety of surgery, as well as reducing surgical time;

(5) to enhance OB/GYN surgery by permitting pristine incision walls, resistance free ablation, microbial sterilization of the ablation site, and bloodless ablations of tissues such a pathologic uterine tissue;

(6) to enhance genital/urinary tract surgeries such as enlarging urinary tract patency, ablation or resection of tumors, ablation or resection of pathologic prostrate tissue;

(7) to enhance ophthalmic surgery as well as ear, nose and throat (ENT) surgery. The eyes and ears in particular are small and highly sensitive structures. The present invention permits pristine incision walls, resistance free ablation, microbial sterilization of the ablation site, bloodless ablations, low power output (e.g., less than 30 Watts), and incision widths in the range often (10) microns;

(8) to enhance dental surgery by permitting pristine incision walls, resistance free ablation, microbial sterilization of the ablation site, and bloodless ablations. The present invention may be used to ablate both oral soft tissue as well as hard tissue such as jaw and teeth;

(9) to enhance neurosurgery by permitting pristine incision walls, resistance free ablation, microbial sterilization of the ablation site, and bloodless ablations. The tissue of the nervous system is highly fragile and sensitive tissue, and thus minimizing collateral damage to surrounding tissue is important; the present invention minimizes such damage. The non-cauterizing hemostasis created by the present invention also has great importance for the brain surgeon since brain tissue is negatively affected by exposure to pools of blood. Microbial disinfection by the plasma cloud helps to further ensure that an infection of the nervous system does not occur postoperatively;

(10) to enhance integument surgery by permitting ablation of skin lesions and anomalies as well as to modify glands that coat the outer surface of the body. This plasma ablation may also create ideal skin pits and skin openings for utilization in hair transplant surgery;

(11) to enhance surgery of the endocrine system wherein pathologic tissue can be removed or ablated in a bloodless, atraumatic fashion. Also, endocrine tissue may be ablated and thereby eliminated while positioned in its natural position without having to excise this tissue first;

(12) to enhance the diagnosis and treatment of specific blood diseases by employing in vivo plasma ablation of the blood within the body or within the vascular tree;

(13) to enhance surgery on pathologic tissue (i.e., tumor surgery) by permitting pristine incision walls, resistance free ablation, microbial sterilization of the ablation site, and bloodless ablations. In particular, the present invention allows a tumor to be removed without 'seeding' the surrounding area with pieces of the tumor (which by themselves can grow and thereby further spread the tumor). The present invention also allows the surgical option of ablating the tumor in its original site, rather than moving the tumor first, as is often done in such procedures;

(14) to enhance surgery on the structures and tissues of the immune system by permitting the ablation of undesirable immunologic structures, thereby eliminating and/or modifying immunologic structures or members in a manner which strengthens or improves the body's immune system, thereby allowing the immune system to have a greater ability to fight off disease and/or prevent disease, therein improving the health of the body;

(15) to enhance surgery on the structures and tissues of the muscle, ligament and tendon systems by permitting the ablation of undesirable muscle, ligament and/or tendon, thereby ridding the body of undesirable or pathologic muscle, ligament and/or tendon tissue. This provides the ability to reshape, realign and/or rebalance the overall force, balance and load carrying capability of the structural framework of the body. Besides improving the overall function of the body, this capability has important implications for pain management, esthetic appearance, etc.;

(16) to enhance the management of microbial organisms including bacteria, fungus, mold, virus, richettsia, prion, etc., in surgery and other medical fields. In particular, microorganisms cannot exist within the plasma cloud of the present invention, and thus the present invention may be used to reduce or eliminate such microorganisms. For example, the present invention may be utilized to decontaminate wounds which have been infected with chemical or biological agents (e.g., mustard gas); and,

(17) to enhance the ablation of other organic matter such as plants or plant products. In particular, the present invention permits the same types of incision in plants, as in biologic tissue.

Although exemplary embodiments of the present invention have been described above for use in procedures involving cardiovascular tissue, those of ordinary skill in the art will realize that the systems 100-300 of the present invention may be used for other types of operations and procedures.

Although the invention has been described in terms of exemplary embodiments, it is not limited thereto. Rather, the appended claims should be construed broadly to include other variants and embodiments of the invention which may be made by those skilled in the art without departing from the scope and range of equivalents of the invention.

What is claimed is:

1. A plasma surgical apparatus for incising a target tissue comprising:
   a radiofrequency signal generator;
   an elongated flexible catheter configured to be inserted in to a blood vessel having a proximal end and a distal end, the proximal end being coupled to a conditioning network and the distal end having a distal end incising electrode tip;
   wherein the catheter includes at least one optic fiber for illumination and image capture;
   wherein the catheter includes an irrigation and an aspiration cannula passageway;
   a conditioning network coupled to the output of the radiofrequency signal generator,
   wherein the conditioning network varies at least one of impedance, frequency, power, or q-curve output to tune radiofrequency energy produced by the radiofrequency signal generator such that the energy is absorbed by the molecular lattice of the target tissue in contact with the distal end incising electrode tip, the molecular bonds of the lattice to fracture, and the fractured molecular particles are transformed into a harmonious plasma cloud, the harmonious plasma cloud coating the distal end incising electrode tip, contributing to the increased concentration of energy in the intended path of incision to achieve a cleaner, more precise, more powerful, and more efficient incision with less energy spillover on non-target tissue outside an intended incision path;
   wherein a plasma fuel is not necessary.

2. The apparatus of claim 1, further comprising at least one power amplifier coupled between the radiofrequency signal generator and the conditioning network.

3. The apparatus of claim 2, further comprising at least one signal gate coupled between the radiofrequency signal generator and the at least one amplifier.

4. The apparatus of claim 1, wherein the conditioning network operates to impedance match an output signal of the apparatus to the harmonious plasma cloud.

5. The apparatus of claim 1, wherein the radiofrequency signal generator operates to frequency match an output signal of the apparatus to the harmonious plasma cloud.

6. The apparatus of claim 2, wherein the at least one power amplifier operates to power match an output signal of the apparatus to the harmonious plasma cloud.

7. The apparatus of claim 1, wherein the conditioning network operates to match the Q-curve of the output signal of the apparatus to the harmonious plasma cloud.

8. The apparatus of claim 1, wherein the radiofrequency signal generator and the conditioning network match an output signal of the conditioning network said target tissue surrounding the distal end incising electrode tip.

9. The apparatus of claim 8, wherein said output signal of said conditioning network generates a conditioned electromagnetic waveform at the at least one electrode which is specifically tuned to said target issue.

10. The apparatus of claim 8, wherein the radiofrequency signal generator and the conditioning network match an output signal of the conditioning network to the harmonious plasma coating the distal end incising electrode tip.

* * * * *

UNITED STATES PATENT AND TRADEMARK OFFICE
CERTIFICATE OF CORRECTION

PATENT NO. : 8,088,126 B2  
APPLICATION NO. : 11/891838  
DATED : January 3, 2012  
INVENTOR(S) : Richard J. Fugo Page 1 of 1

It is certified that error appears in the above-identified patent and that said Letters Patent is hereby corrected as shown below:

Title page, item (*) Notice should read: this patent is not subjected to a terminal disclaimer or terminal disclaimer limitations.

Signed and Sealed this
Third Day of July, 2012

David J. Kappos
*Director of the United States Patent and Trademark Office*